United States Patent
Long et al.

(10) Patent No.: US 10,743,573 B2
(45) Date of Patent: Aug. 18, 2020

(54) **METHOD FOR EXTRACTING HIGH-PURITY MOGROSIDE V FROM *SIRAITIA GROSVENORII***

(71) Applicant: Jiangxi Haifu Bioengineering Co., Ltd., Yichun, Jiangxi (CN)

(72) Inventors: Weian Long, Hunan (CN); Huaxue Huang, Hunan (CN)

(73) Assignee: Jiangxi Haifu Bioengineering Co., Ltd., Yichun, Jiangxi (CN)

( * ) Notice: Subject to any disclaimer, the term of this patent is extended or adjusted under 35 U.S.C. 154(b) by 99 days.

(21) Appl. No.: 16/307,309

(22) PCT Filed: Jan. 4, 2017

(86) PCT No.: PCT/CN2017/070140
§ 371 (c)(1),
(2) Date: Dec. 5, 2018

(87) PCT Pub. No.: WO2017/211079
PCT Pub. Date: Dec. 14, 2017

(65) Prior Publication Data
US 2019/0133166 A1    May 9, 2019

(30) Foreign Application Priority Data
Jun. 6, 2016  (CN) .......................... 2016 1 0387839

(51) Int. Cl.
| | | |
|---|---|---|
| *A61K 36/00* | (2006.01) | |
| *A23L 27/30* | (2016.01) | |
| *B01D 61/58* | (2006.01) | |
| *C07J 17/00* | (2006.01) | |
| *B01D 61/02* | (2006.01) | |
| *B01D 61/14* | (2006.01) | |

(52) U.S. Cl.
CPC .............. *A23L 27/36* (2016.08); *B01D 61/58* (2013.01); *C07J 17/005* (2013.01); *A23V 2002/00* (2013.01); *A23V 2300/10* (2013.01); *A23V 2300/14* (2013.01); *A23V 2300/24* (2013.01); *A23V 2300/34* (2013.01); *A23V 2300/38* (2013.01); *B01D 61/027* (2013.01); *B01D 61/145* (2013.01); *B01D 2311/04* (2013.01); *B01D 2311/06* (2013.01); *B01D 2311/08* (2013.01)

(58) Field of Classification Search
None
See application file for complete search history.

(56) References Cited

U.S. PATENT DOCUMENTS 6,124,442 A    9/2000    Zhou et al.

FOREIGN PATENT DOCUMENTS

| CN | 1683387 A | 10/2005 | |
|---|---|---|---|
| CN | 101177444 A | 5/2008 | |
| CN | 100572552 C | 12/2009 | |
| CN | 101007042 B | 5/2010 | |
| CN | 101863946 A | 10/2010 | |
| CN | 101690573 B | 1/2012 | |
| CN | 104558088 A | 4/2015 | |
| CN | 105218612 A | 1/2016 | |
| EP | 2425721 A1 | 3/2012 | |
| WO | WO-2008030121 A1 * | 3/2008 | ............... A23L 2/60 |

OTHER PUBLICATIONS

Tang et al., The New Technology of Extracting Biological Activity Substance High Purity Mogroside V from Grosvenor Momordica Fruit, Applied Technology, Enterprise Science and Technology & Development No. 8, 2012 (Cumulatively No. 326): the year of publication is sufficiently earlier than the effective U.S. filing date and any foreign priority date.

\* cited by examiner

*Primary Examiner* — Qiuwen Mi
(74) *Attorney, Agent, or Firm* — Bret E. Field; Bozicevic, Field & Francis LLP

(57) ABSTRACT

The present application relates to a technique for extracting mogroside V. Provided is a method for extracting high-purity mogroside V from *Siraitia grosvenorii*. The specific steps comprise: pre-treatment of a raw material, extraction, centrifugation, enzymolysis, ultrafiltration, nanofiltration, decolorization, concentration, microwave drying, and pulverization. The invention utilizes a membrane-based technique for separation and purification, and only uses pure water as a solvent to eliminate usage of an organic solvent. The method can be easily performed, has a simple process, and provides a safe, environment-friendly, high quality, and low-cost product. The method can be used to realize continuous large-scale industrial production.

10 Claims, No Drawings

METHOD FOR EXTRACTING HIGH-PURITY MOGROSIDE V FROM *SIRAITIA GROSVENORII*

The present application claims priority to Chinese Patent Application No. 201610387839.4, entitled "METHOD FOR EXTRACTING HIGH-PURITY MOGROSIDE V FROM *SIRAITIA GROSVENORII*", filed to Chinese National Intellectual Property Administration on Jun. 6, 2016, which is incorporated herein by reference in its entirety.

FIELD OF TECHNOLOGY

The present application relates to the technical field of a method for extracting mogroside V, and in particular, to a method for extracting high-purity mogroside V from Luo Han Guo.

BACKGROUND

Luo Han Guo (whose Latin name is *Siraitia grosvenorii*) is a kind of perennial lianas belonging to the family Cucurbitaceae. Luo Han Guo is dioecious. It has heart-shaped leaves, blooms in summer and bears fruit in autumn. The fruit of Luo Han Guo contains medicinal ingredients such as mogroside, a variety of amino acids, vitamins and so on. In traditional Chinese Medicine, the fruit of Luo Han Guo can be used as a medicine to treat cough caused by lung heat, laryngopharyngitis, amygdalitis, acute gastritis, constipation and so on. Luo Han Guo is also known as a sweetener. It is widely used as a sweetening agent due to high sweetness and low calorie. Generally, Luo Han Guo is used as a substitute of sugar for patients with obese or diabetics.

Patent No. CN200910044558.9 provides a method for producing Luo Han Guo extract with the content of mogroside V being more than 60%. The process flow is crushing-→saccharification→water extraction→concentration→centrifugal sedimentation→ion exchange resin refinement→macroporous resin refinement→concentration→alumina refinement→concentration→spray drying→end product. The method has a long process route, and a serial combination of macroporous resin and alumina is needed in separation and purification. Besides, the operation is complicated and the cost is high.

Patent No. CN200710003364.5 discloses a method for preparing Luo Han Guo extract which is decolorized and debitterized. In the method, the extracted liquid is filtrated, concentrated, decolorized with decolorizing resin and then eluted with ethanol, and debitterized with deodorant; afterward, concentration, spray drying and pulverization are performed to obtain the Luo Han Guo extract which is decolorized and debitterized. The weight content of mogroside V in the Luo Han Guo extract is 60% and more (HPLC). In this invention, macroporous resin is needed for adsorption and purification during separation and purification, and subsequently, an organic solvent is used for elution. Therefore, the operation is complicated and has a problem of solvent residue, and the cost is high.

Patent No. CN200710049737.2 provides a method for preparing milky white Luo Han Guo extract with the content of mogroside V being 40% or more and the content of mogroside being 98% or more. The method comprises steps of water extraction—concentration—enzymolysis—macroporous resin refinement—ion exchange resin decolorization—concentration—spray drying. In this invention, macroporous resin is needed for adsorption and purification during separation and purification, and subsequently, an organic solvent is used for elution. Therefore, the operation is complicated and has a problem of solvent residue, and the cost is high.

Currently, separation and purification of mogroside V mainly comprises the steps of using macroporous resin for adsorption, using different solvents for elution so as to obtain a crude extract with a certain amount of mogroside V, subjecting the crude extract to desalination and decolorization, and finally drying, sieving and packing the product. Besides, preparative chromatography and high speed countercurrent chromatography may also be used. Column chromatography is the most widely used, and macroporous adsorptive resins, such as resin type of D101 and AB-8, are most commonly used in the separation and purification. However, the operation of separation and purification with macroporous adsorptive resins is complicated, the yield of mogroside V is low, and the use of an organic solvent in elution leads to problems of solvent residue and environmental pollution. Although preparative chromatography and high speed countercurrent chromatography can achieve a high product content, equipment disposable investment is huge, the consumption of organic solvent is large, and problems such as solvent residue and environmental pollution still exist.

SUMMARY

The present application provides a method for extracting high-purity mogroside V from Luo Han Guo. The method can increase the purity of mogroside V extracted from fresh Luo Han Guo from 0.3~0.5% to 50% or more, so that the above technical problem can be solved.

In the first aspect, the present application provides a preparation method for extracting high-purity mogroside V from Luo Han Guo. The method comprises:

(1) pre-treatment of raw material: crushing the raw material by using a crusher in accordance with the standard of one fresh fruit being broken into 6 to 10 pieces;

(2) extraction: using hot water to continuous countercurrent extract mogroside V from the raw material obtained in step (1) by means of continuous countercurrent extraction method, subjecting the raw material obtained in step (1) to hot water continuous countercurrent extraction to extract mogroside V; and passing the extracted liquid through a 200 to 400-mesh stainless steel sieve to obtain a filtrate;

(3) centrifugation: subjecting the filtrate obtained in step (2) to centrifugal filtration to obtain a centrifugate;

(4) enzymolysis: cooling down the centrifugate obtained in step (3), subsequently delivering it to an enzymolysis tank, and adding an enzyme reagent therein to perform enzymolysis;

(5) ultrafiltration: passing the enzymatic centrifugate obtained in step (4) through an ultrafiltration membrane to concentrate to small-volume solution, adding water therein to perform dialysis until the conductivity of the solution meeting the requirement, and obtaining a filtrate;

(6) nanofiltration: using a nanofiltration membrane to separate and purify the filtrate obtained in step (5), concentrating it to small-volume solution, adding water therein to perform dialysis until the conductivity of the solution meeting the requirement, and obtaining an intercepted liquid;

(7) decolorization: using a decolorizing resin column to decolorize the intercepted liquid obtained in step (6), collecting the effluent liquid flowing through the resin column after decolorization, and obtaining a decolorized liquid;

(8) concentration: subjecting the decolorized liquid obtained in step (7) to vacuum concentration under a pressure controlled in the range of −0.1~0.06 MPa and a temperature controlled in the range of 40~50° C. until the solid content is in the range 40~60%, and obtaining a concentrated liquid; and (9) microwave drying and pulverization: subjecting the concentrated liquid obtained in step (9) to microwave drying, pulverizing and sieving, and finally packing.

Combined with the first aspect and in the first possible embodiment of the first aspect, in step (1), the raw material is a saccharified fresh fruit of Luo Han Guo without any other Impurity, and the degree of crushing is to break one fruit into 6 to 10 pieces.

Combined with the first aspect and in the second possible embodiment of the first aspect, in step (2), the extraction method is a continuous countercurrent extraction method, and the continuous countercurrent extraction is performed for 1~2 hours by using 95~99° C. hot water which is twice to four times as weight as the fresh fruit.

Combined with the first aspect and in the third possible embodiment of the first aspect, in step (3), the centrifugation is performed by a combination of an horizontal centrifuge with a disk-bowl centrifuge or a tube centrifuge, and the centrifugation speed is controlled in the range of 10000~50000 r/min.

Combined with the first aspect and in the fourth possible embodiment of the first aspect, in step (4), the enzyme reagent used in the step of enzymolysis is a liquid enzyme provided by Novozymes, the additive amount of the enzyme reagent is in the range of 0.01~0.03 w/v % of the volume of the extracted liquid, the enzymolysis temperature is in the range of 30~50° C., the enzymolysis time is in the range of 2~4 hours, and the enzymolysis pH is in the range of 3~6.

Combined with the first aspect and in the fifth possible embodiment of the first aspect, in step (5), the ultrafiltration membrane has a molecular weight in the range of 80000~100000 Dalton, and the ultrafiltration is performed under a pressure in the range of 1.0~2.0 MPa and a temperature controlled in the range of 10~25° C. until the conductivity of the filtrate is 500 μs/cm or less.

Combined with the first aspect and in the sixth possible embodiment of the first aspect, in step (6), the nanofiltration membrane has a molecular weight in the range of 600~5000 Dalton, the nanofiltration is performed under a pressure controlled in the range of 2.0~4.0 MPa and a temperature controlled in the range of 10~25° C., and the solid content in the intercepted liquid is in the range of 10%~30% and the conductivity of the intercepted liquid is 500 μs/cm or less.

Combined with the first aspect and in the seventh possible embodiment of the first aspect, in step (7), the decolorizing resin column is D941, LSA-700, or DA201-H.

Combined with the first aspect and in the eighth possible embodiment of the first aspect, in step (8), the concentration is performed by a single-effect, double-effect or three-effect concentrator.

Combined with the first aspect and in the ninth possible embodiment of the first aspect, in step (9), the microwave drying is performed under a pressure controlled in the range of −0.1~0.06 MPa and a temperature in the range of 40~50° C., and the water content of a final product is controlled to be less than 5%.

The invention has the following advantages:

1) The invention uses water as an extraction solvent and employs a continuous countercurrent extraction method. Compared with an extraction method using an extraction tank, the invention can reduce water consumption, shorten extraction time, save energy, and achieve continuous large-scale production.

2) In the invention, the permeating liquid obtained after separation and purification by the nanofiltration membrane and the water obtained after concentration and recovery can be fed back as the extraction solvent. Thus, water resource can be saved and almost no sewage discharges, so that good environment protection can be ensured.

3) The invention utilizes a membrane-based technique for separation and purification. Compared with other purification methods such as macroporous resin adsorption for purification, the invention has the advantages of providing obvious effects of separation and purification and only using pure water as a solvent to eliminate usage of an organic solvent. Besides, the invention can be easily performed, and can provide a safe, environment-friendly, high quality, and low-cost product through simple process. The invention can be also used to realize continuous large-scale industrial production.

DESCRIPTION OF THE EMBODIMENTS

The same or similar parts of the examples in the description could refer to each other.

Example 1

1) Pre-treatment of raw material: 1000 Kg of a fresh fruit raw material with impurities removed were crushed by using a crusher, and simultaneously, the crushed materials were added into a continuous countercurrent extraction machine.

2) Extraction: 2000 Kg of 96° C. hot pure water was added reversely at the same time so as to perform continuous countercurrent extraction, and the extraction time was set to 1 hour.

3) Centrifugation: the filtrate obtained in step (2) was centrifugated in a horizontal centrifuge, cooled down to 30° C., and then passed through a disk-bowl centrifuge to obtain 2158 kg of a centrifugate with a temperature of 32° C.

4) Enzymolysis: the 2158 kg of the centrifugate obtained in step (3) was delivered into a enzymolysis tank, and then a complex enzyme (a kind of liquid enzyme purchased from Novozymes) of cellulose, pectinase and protease was added to perform enzymolysis. The additive amount of the complex enzyme is 0.01% of the volume of the extracted liquid, the enzymolysis temperature is controlled at 32° C., the time of the enzymolysis is controlled to be 2 hours, and the pH of enzymolysis is 4.5.

5) Ultrafiltration: the enzymatic hydrolysate obtained in step (4) was passed through an ultrafiltration membrane with a molecular weight of 80000~100000 Dalton and the pressure of the ultrafiltration membrane was controlled at 1.2 MPa. The temperature of the enzymatic hydrolysate was controlled at 15° C. by using a cooling plate. Ultrafiltration continued until the flow speed of the filtrate was ⅟10 of the starting speed, and then 500 L pure water was added therein to perform dialysis. The foregoing operations were repeated for three times until the conductivity of the filtrate was 500 μs/cm or less, and then the filtrate was collected.

6) nanofiltration: 3318 kg of the filtrate obtained in step (5) was separated and purified by using a nanofiltration membrane with a molecular weight of 600~1000 Dalton and the pressure of the ultrafiltration membrane was controlled at 2.0 MPa. The temperature of the materiel was controlled at 15° C. when performing filtration. When the flow speed of the filtrate was ⅟10 of the starting speed, 500 L pure water was added to perform dialysis. The foregoing operations were repeated for three times until the conductivity of the filtrate was 500 μs/cm or less, and then the nanofiltration solution was obtained by collecting the intercepted liquid within the membrane.

7) Decolorization: 268 kg of the nanofiltration solution obtained in step (6) was decolorized by using a decolorizing resin column to collect the effluent liquid flowing through the decolorizing resin column after decolorization. After all the materials were passed through the decolorizing resin column, pure water with a volume being two times of the column volume was used to remove the sweet taste of the effluent liquid. The decolorized liquid was obtained by collecting the effluent liquid.

8) Concentration: 280 kg of the decolorized liquid obtained in step (7) was concentrated under vacuum by using a single-effect concentrator with the vacuum pressure controlled at −0.086 MPa and at a temperature of 45° C., and 30.5 Kg of concentrated liquid was obtained.

9) Microwave drying: the concentrated liquid was subjected to microwave drying with the pressure controlled at −0.08 MPa at a drying temperature of 40° C., and the water content of the final product was controlled to be less than 5%. The final product weighed 16.38 Kg, and the content of mogroside V was 50.1% (HPLC).

Example 2

1) Pre-treatment of raw material: 1000 Kg of a fresh fruit raw material with impurities removed were crushed by using a crusher, and simultaneously, the crushed materials were added into a continuous countercurrent extraction machine.

2) Extraction: 3000 Kg of 98° C. hot pure water was added reversely at the same time so as to perform continuous countercurrent extraction, and the extraction time was set to 1.5 hours.

3) Centrifugation: the filtrate obtained in step (2) was centrifugated in a horizontal centrifuge, cooled down to 35° C., and then passed through a disk-bowl centrifuge to obtain 3080 kg of a centrifugate with a temperature of 38° C.

4) Enzymolysis: the 3080 kg of the centrifugate obtained in step (3) was delivered into a enzymolysis tank, and then a complex enzyme (a kind of liquid enzyme purchased from Novozymes) of cellulose, pectinase and protease was added to perform enzymolysis. The additive amount of the complex enzyme is 0.02% of the volume of the extracted liquid, the enzymolysis temperature is controlled at 38° C., the time for enzymolysis is controlled to be 3 hours, and the pH of enzymolysis is 4.8.

5) Ultrafiltration: the enzymatic hydrolysate obtained in step (4) was passed through an ultrafiltration membrane with a molecular weight of 80000~100000 Dalton and the pressure of the ultrafiltration membrane was controlled at 1.6 MPa. The temperature of the enzymatic hydrolysate was controlled at 15° C. by using a cooling plate. Ultrafiltration continued until the flow speed of the filtrate was 1/10 of the starting speed, and then 500 L pure water was added therein to perform dialysis. The foregoing operations were repeated for three times until the conductivity of the filtrate was 500 μs/cm or less, and then the filtrate was collected.

6) nanofiltration: 4018 kg of the filtrate obtained in step (5) was separated and purified by using a nanofiltration membrane with a molecular weight of 600~1000 Dalton and the pressure of the ultrafiltration membrane was controlled at 3.0 MPa. The temperature of the materiel was controlled at 15° C. when performing filtration. When the flow speed of the filtrate was 1/10 of the starting speed, 500 L pure water was added to perform dialysis. The foregoing operations were repeated for three times until the conductivity of the filtrate was 500 μs/cm or less, and then the nanofiltration solution was obtained by collecting the intercepted liquid within the membrane.

7) Decolorization: 276 kg of the nanofiltration obtained in step (6) was decolorized by using a decolorizing resin column to collect the effluent liquid flowing d through the decolorizing resin column. After all the materials were passed through the decolorizing resin column, pure water with a volume being two times of the column volume was used to remove the sweet taste of the effluent liquid. The decolorized liquid was obtained by collecting the effluent liquid.

8) Concentration: 284 kg of the decolorized liquid obtained in step (7) was concentrated under vacuum by using a single-effect concentrator with the vacuum pressure controlled at −0.086 MPa and the temperature being 45° C., and 31.2 Kg of concentrated liquid was obtained.

9) Microwave drying: the concentrated liquid was subjected to microwave drying with the pressure controlled at −0.085 MPa and a drying temperature being 45° C., and the water content of the final product was controlled to be less than 5%. The final product weighed 16.28 Kg, and the content of mogroside V was 50.7% (HPLC).

Example 3

1) Pre-treatment of raw material: 1000 Kg of a fresh fruit raw material with impurities removed were crushed by using a crusher, and simultaneously, the crushed materials were added into a continuous countercurrent extraction machine.

2) Extraction: 4000 Kg of 98° C. hot pure water was added reversely at the same time so as to perform continuous countercurrent extraction, and the extraction time was set to 1.5 hours.

3) Centrifugation: the filtrate obtained in step (2) was centrifugated in a horizontal centrifuge, cooled down to 42° C., and then passed through a disk-bowl centrifuge to obtain 4176 kg of a centrifugate with a temperature of 44° C.

4) Enzymolysis: the 4176 kg of the centrifugate obtained in step (3) was delivered into a enzymolysis tank, and then a complex enzyme (a kind of liquid enzyme purchased from Novozymes) of cellulose, pectinase and protease was added to perform enzymolysis. The additive amount of the complex enzyme is 0.03% of the volume of the extracted liquid, the enzymolysis temperature is controlled at 44° C., the time for enzymolysis is controlled to be 4 hours, and the pH of enzymolysis is 5.3.

5) Ultrafiltration: the enzymatic hydrolysate obtained in step (4) was passed through an ultrafiltration membrane with a molecular weight of 80000~100000 Dalton and the pressure of the ultrafiltration membrane was controlled at 2.0 MPa. The temperature of the enzymatic hydrolysate was controlled at 15° C. by using a cooling plate. Ultrafiltration continued until the flow speed of the filtrate was 1/10 of the starting speed, and then 500 L pure water was added therein to perform dialysis. The foregoing operations were repeated for three times until the conductivity of the filtrate was 500 μs/cm or less, and then the filtrate was collected.

6) nanofiltration: 5708 kg of the filtrate obtained in step (5) was separated and purified by using a nanofiltration membrane with a molecular weight of 600~1000 Dalton and the pressure of the ultrafiltration membrane was controlled at 3.5 MPa. The temperature of the materiel was controlled at 15° C. when performing filtration. When the flow speed of the filtrate was 1/10 of the starting speed, 500 L pure water was added to perform dialysis. The foregoing operations were repeated for three times until the conductivity of the filtrate was 500 μs/cm or less, and then the nanofiltration solution was obtained by collecting the intercepted liquid within the membrane.

7) Decolorization: 280 kg of the nanofiltration obtained in step (6) was decolorized by using a decolorizing resin column to collect the effluent liquid flowing through the decolorizing resin column. After all the materials were passed through the resin, pure water with a volume being two times of the column volume was used to remove the sweet taste of the effluent liquid. The decolorized liquid was obtained by collecting the effluent liquid.

8) Concentration: 291 kg of the decolorized liquid obtained in step (7) was concentrated under vacuum by using a single-effect concentrator with the vacuum pressure controlled at −0.09 MPa and the temperature being 45° C., and 32.1 Kg concentrated liquid was obtained.

9) Microwave drying: the concentrated liquid was subjected to microwave drying with the pressure controlled at −0.09 MPa and a drying temperature being 50° C., and the water content of the final product was controlled to be less than 5%. The final product weighed 16.50 Kg, and the content of mogroside V was 50.5% (HPLC).

The above embodiments of the invention shall not be construed as limiting the scope of the invention.

What is claimed is:

1. A preparation method for extracting high-purity mogroside V from Luo Han Guo, characterized in that, the method comprises the following steps:
   (1) pre-treatment of raw material: crushing a raw material by using a crusher in accordance with the standard of one fresh fruit being broken into 6 to 10 pieces;
   (2) extraction: by means of continuous countercurrent extraction method, subjecting the raw material obtained in step (1) to hot water continuous countercurrent extraction to extract mogroside V; and passing the extracted liquid through a 200 to 400-mesh stainless steel sieve to obtain a filtrate;
   (3) centrifugation: subjecting the filtrate obtained in step (2) to centrifugal filtration to obtain a centrifugate;
   (4) enzymolysis: cooling down the centrifugate obtained in step (3), subsequently delivering it to an enzymolysis tank, and adding an enzyme reagent therein to perform enzymolysis;
   (5) ultrafiltration: passing the enzymatic centrifugate obtained in step (4) through an ultrafiltration membrane to concentrate to small-volume solution, adding water therein to perform dialysis until the conductivity of the solution meeting the requirement, and obtaining a filtrate;
   (6) nanofiltration: using a nanofiltration membrane to separate and purify the filtrate obtained in step (5), concentrating it to small-volume solution, adding water therein to perform dialysis until the conductivity of the solution meeting the requirement, and obtaining an intercepted liquid;
   (7) decolorization: using a decolorizing resin column to decolorize the intercepted liquid obtained in step (6), collecting the effluent liquid flowing through the decolorizing resin column after decolorization, and obtaining a decolorized liquid;
   (8) concentration: subjecting the decolorized liquid obtained in step (7) to vacuum concentration with a pressure controlled in the range of −0.1~0.06 MPa and a temperature controlled in the range of 40~50° C. until solid content is in the range of 40~60%, and obtaining a concentrated liquid; and
   (9) microwave drying and pulverization: subjecting the concentrated liquid obtained in step (9) to microwave drying, pulverizing and sieving, and finally packing.

2. The preparation method for extracting high-purity mogroside V from Luo Han Guo according to claim 1, characterized in that, in step (1), the raw material is a saccharified fresh fruit of Luo Han Guo without any other impurity, and the degree of crushing is to break one fruit into 6 to 10 pieces.

3. The preparation method for extracting high-purity mogroside V from Luo Han Guo according to claim 1, characterized in that, in step (2), the extraction method is a continuous countercurrent extraction method, and the continuous countercurrent extraction is performed for 1~2 hours by using 95~99° C. hot water which is twice to four times as weight as the fresh fruit.

4. The preparation method for extracting high-purity mogroside V from Luo Han Guo according to claim 1, characterized in that, in step (3), the centrifugation is performed by a combination of an horizontal centrifuge with a disk-bowl centrifuge or a tube centrifuge, and the centrifugation speed is controlled in the range of 10000~50000 r/min.

5. The preparation method for extracting high-purity mogroside V from Luo Han Guo according to claim 1, characterized in that, in step (4), the enzyme reagent used in the step of enzymolysis is a liquid enzyme provided by Novozymes, the additive amount of the enzyme reagent is in the range of 0.01~0.03 w/v % of the volume of the extracted liquid, the enzymolysis temperature is in the range of 30~50° C., the enzymolysis time is in the range of 2~4 hours, and the enzymolysis pH is in the range of 3~6.

6. The preparation method for extracting high-purity mogroside V from Luo Han Guo according to claim 1, in step (5), the ultrafiltration membrane has a molecular weight cutoff in the range of 80000~100000 Dalton, and the ultrafiltration is performed under a pressure in the range of 1.0~2.0 MPa and a temperature being controlled in the range of 10~25° C. until the conductivity of the filtrate is 500 μs/cm or less.

7. The preparation method for extracting high-purity mogroside V from Luo Han Guo according to claim 1, in step (6), the nanofiltration membrane has a molecular weight cutoff in the range of 600~5000 Dalton, the nanofiltration is performed under a pressure controlled in the range of 2.0~4.0 MPa and a temperature controlled in the range of 10~25° C., and the solid content in the intercepted liquid is in the range of 10%~30% and the conductivity of the intercepted liquid is 500 μs/cm or less.

8. The preparation method for extracting high-purity mogroside V from Luo Han Guo according to claim 1, in step (7), the decolorizing resin column is D941, LSA-700, or DA201-H.

9. The preparation method for extracting high-purity mogroside V from Luo Han Guo according to claim 1, in step (8), the concentration is performed by a single-effect, double-effect or three-effect concentrator.

10. The preparation method for extracting high-purity mogroside V from Luo Han Guo according to claim 1, in step (9), the microwave drying is performed under a pressure controlled in the range of −0.1~0.06 MPa and a drying temperature in the range of 40~50° C., and the water content of a final product is controlled to be less than 5%.

* * * * *